United States Patent [19]
Imran et al.

[11] Patent Number: 5,465,717
[45] Date of Patent: Nov. 14, 1995

[54] APPARATUS AND METHOD FOR VENTRICULAR MAPPING AND ABLATION

[75] Inventors: Mir A. Imran, Palo Alto; Mark L. Pomeranz, Los Gatos; Gholam-Reza Zadno-Azizi, Newark, all of Calif.

[73] Assignee: Cardiac Pathways Corporation, Sunnyvale, Calif.

[21] Appl. No.: 290,391

[22] Filed: Aug. 15, 1994

Related U.S. Application Data

[63] Continuation of Ser. No. 44,255, Apr. 7, 1993, abandoned, which is a continuation-in-part of Ser. No. 983,968, Dec. 1, 1992, Pat. No. 5,327,889, which is a continuation-in-part of Ser. No. 656,764, Feb. 15, 1991, Pat. No. 5,156,151.

[51] Int. Cl.$^6$ ............................. A61B 5/04; A61N 1/05
[52] U.S. Cl. ............................................. 128/642; 607/122
[58] Field of Search ........................... 128/642; 607/115, 607/116, 119, 122, 123, 126, 128, 130

[56] References Cited

U.S. PATENT DOCUMENTS

| | | | |
|---|---|---|---|
| 4,522,212 | 6/1985 | Gelinas et al. | 128/642 |
| 4,592,372 | 6/1986 | Beranek | 607/119 |
| 4,660,571 | 4/1987 | Hess et al. | 607/119 |
| 4,699,147 | 10/1987 | Chilson et al. | 607/119 X |
| 4,940,064 | 7/1990 | Desai | 607/119 |
| 5,010,894 | 4/1991 | Edhag | 607/119 |
| 5,127,421 | 7/1992 | Bush et al. | 607/119 X |
| 5,237,996 | 8/1993 | Waldman et al. | 128/642 |

OTHER PUBLICATIONS

Zadno, et al., "Linear and non–linear superelasticity in NiTi"; MRS Int'l Mtg. on Adv. Mats. vol. 9, 1989 Materials Research Society, pp. 201–206.

Duerig, et al., "An engineer's perspective of pseudoelasticity," pp. 369–393, *Engineering aspects of shape memory alloys*, Butterworth–Heinemann, pub. 1990.

*Primary Examiner*—Lee S. Cohen
*Assistant Examiner*—Jeffrey R. Jastrzab
*Attorney, Agent, or Firm*—Flehr, Hohbach, Test, Albritton & Herbert; Harold C. Hohbach

[57] ABSTRACT

Apparatus for mapping a wall of a heart forming a chamber in the heart comprising a guiding catheter having a lumen extending therethrough and a mapping catheter having a shaft that is slidably mounted in the lumen of the guiding catheter. A basket assembly is provided and is comprised of a plurality of circumferentially spaced-apart longitudinally extending arms having proximal and distal extremities. The proximal extremities of the arms are secured to the distal extremity of the shaft of the mapping catheter. Each of the arms includes a member formed of a material having a recoverable strain in excess of 1% and has an outwardly bowed shape memory. At least one electrode is provided on each of the arms. Conductors connected to the electrodes are carried by the arms.

29 Claims, 7 Drawing Sheets

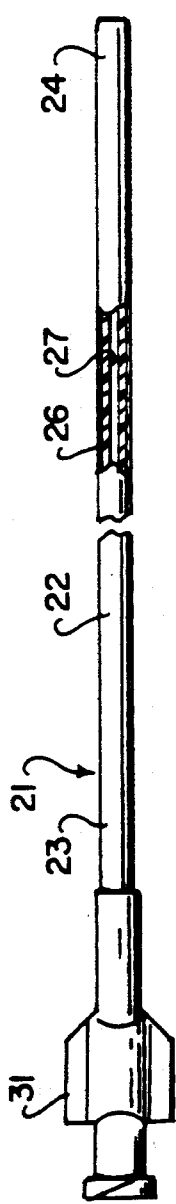
FIG.1
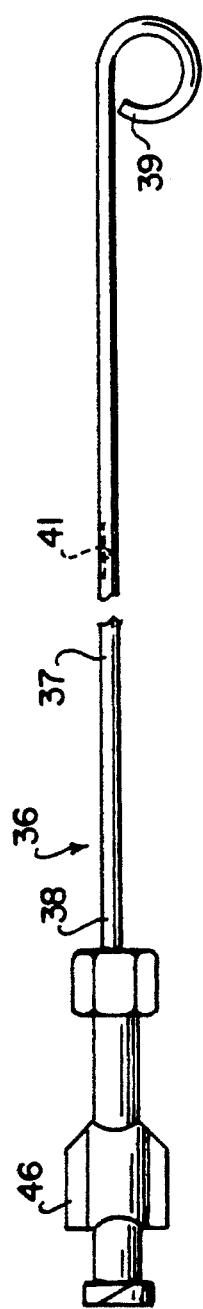
FIG.2
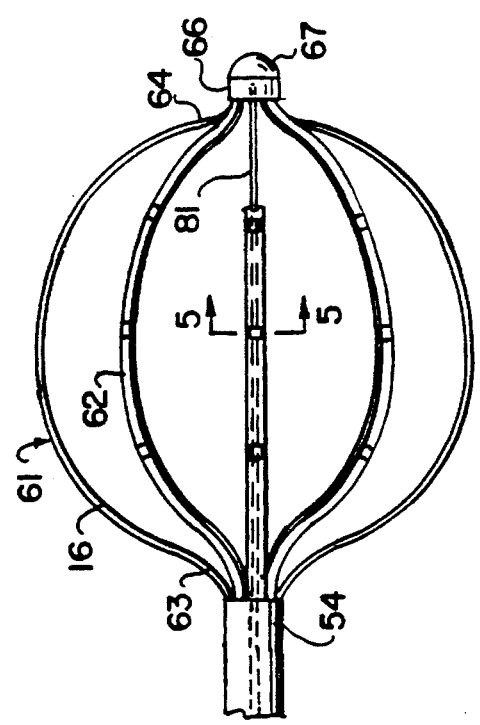
FIG.3
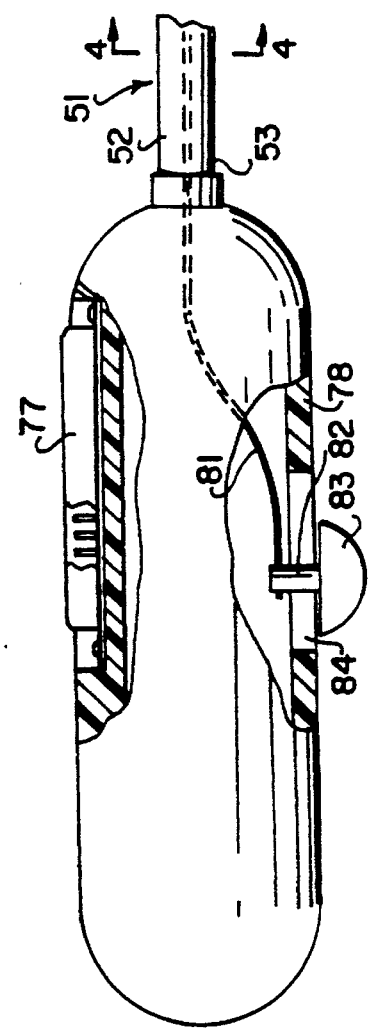

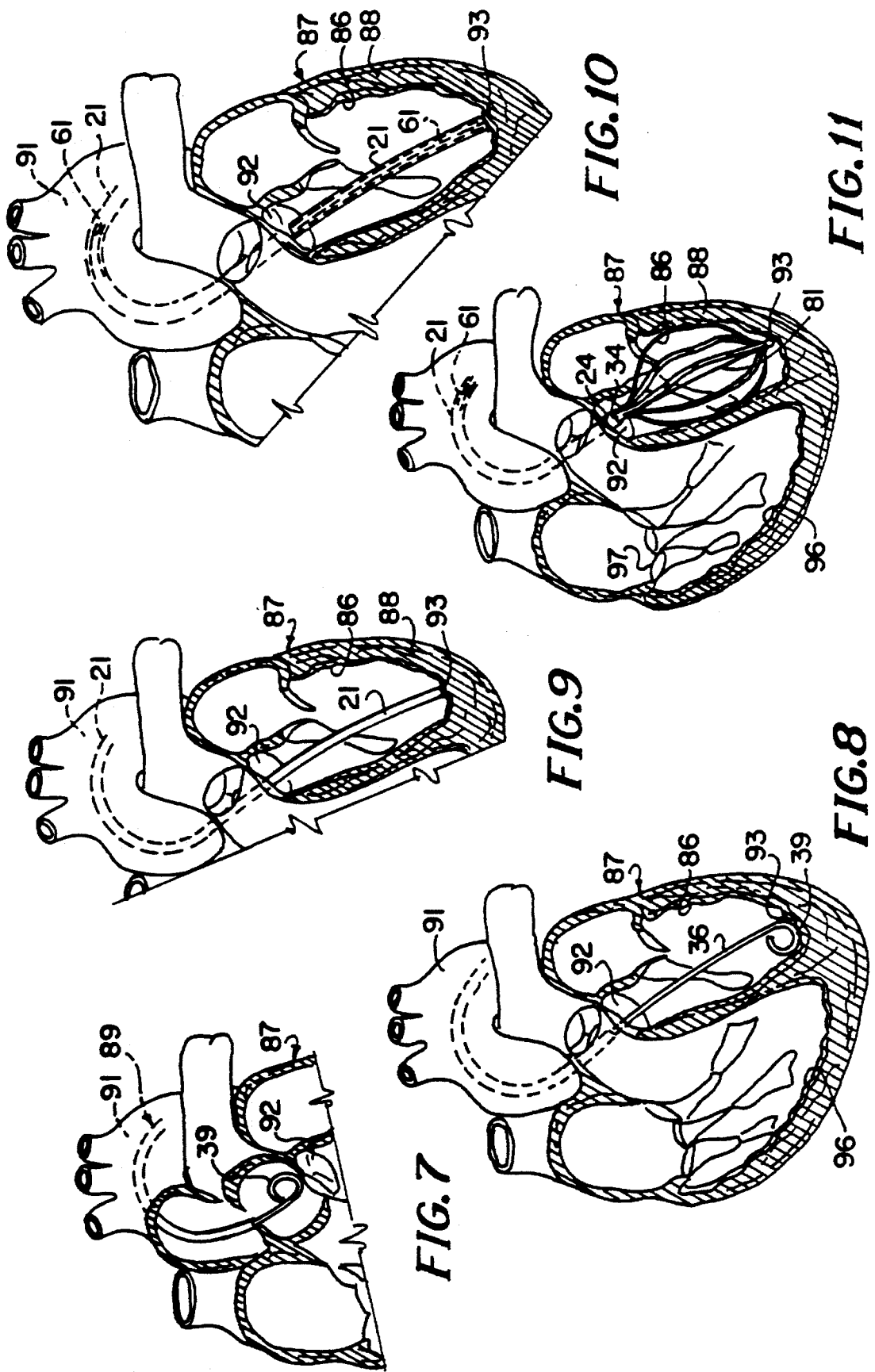

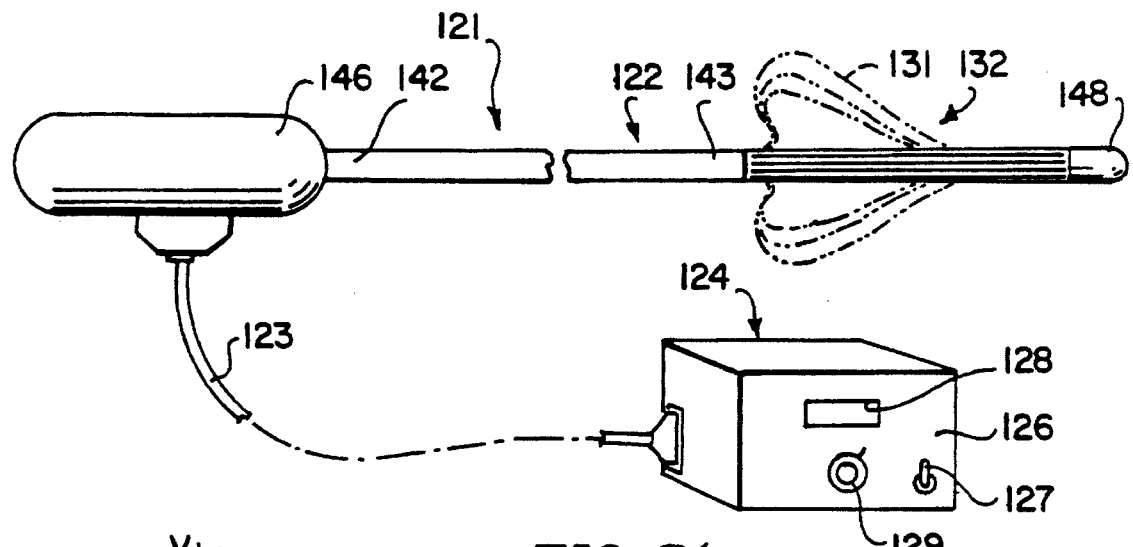
*FIG. 21*
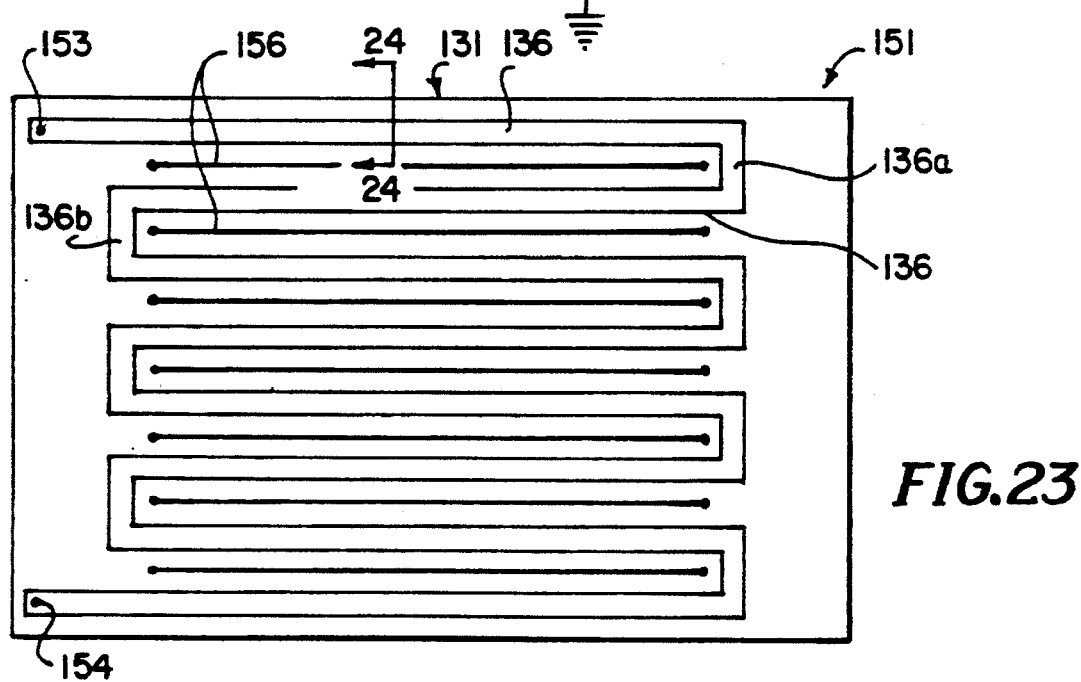
*FIG. 22*
*FIG. 23*

APPARATUS AND METHOD FOR VENTRICULAR MAPPING AND ABLATION

This is a continuation, of application Ser. No. 08/044,255 filed Apr. 7, 1993, now abandoned which is a continuation-in-part of application Ser. No. 07/983,968 filed on Dec. 1, 1992 now U.S. Pat. No. 5,327,889, which is a continuation-in-part of application Ser. No. 07/656,764 filed on Feb. 15, 1991 now U.S. Pat. No. 5,156,151.

In general, the object of the present invention is to provide an apparatus and method which is suitable for ventricular mapping.

Endocardial mapping catheters have hereinbefore been provided. However, they have been of limited capability particularly because they only have a small number of electrodes which makes it difficult to accurately map the electrical potentials in the walls from the chambers of the heart as for example the left ventricle. With such catheters, it is often been necessary to manuver the distal extremity of the catheter extensively and to reposition it incrementally self circumferentially in the chamber of the heart. Such procedures are time consuming and are relatively inaccurate because such measurements take place over more than one heart beat. For that reason it has been difficult to properly characterize the electrical potentials which have been derived from the heart. There is therefore need for a new and improved endocardial mapping apparatus and method for accomplishing the same.

This invention relates to an apparatus and method for ventricular mapping and ablation.

Another object of the invention is to provide an apparatus and method in which deployment can be readily accomplished.

Another object of the invention is to provide an apparatus and method in which the basket has arms that yieldably engage the wall of the heart.

Another object of the invention is to provide an apparatus and method of the above character in which the arms along substantially the entire length thereof remain in engagement with the wall of the heart during beating of the heart without waisting occurring.

Another object of the invention is to provide an apparatus and method of the above character in which the material utilized in the basket has elastic properties.

Another object of the invention is to provide an apparatus of the above character in which the material utilized is stress activated.

Another object of the invention is to provide an apparatus of the above character which is thermally activated.

Another object of the invention is to provide an apparatus of the above character in which the basket is formed of a material which is superelastic at any temperature in the range of 15° C.–50° C.

Additional objects and features of the invention will appear from the following description in which the preferred embodiments are set forth in detail in conjunction with the company drawings.

FIG. 1 is a side-elevational view of a guiding catheter utilized in conjunction with the present invention.

FIG. 2 is a side-elevational view of a pigtail catheter utilized in conjunction with the present invention.

FIG. 3 is a side-elevational view of a mapping catheter incorporating in the present invention with the basket in an expanded position.

FIGS. 7, 8, 9, 10 and 11 are cross-sectional views of a heart showing the manner in which the apparatus of the present invention is utilized in performing the method of the present invention to conduct a mapping operation.

FIG. 21 is a isometric view of another embodiment of a ventricular mapping apparatus incorporated in the present invention.

FIG. 22 is a circuit diagram showing certain of the circuitry used in the apparatus shown in FIG. 21.

FIG. 23 is a plan view of a sheet of plastic utilized for making a basket for use in the apparatus shown in FIG. 21.

Figure 5A:
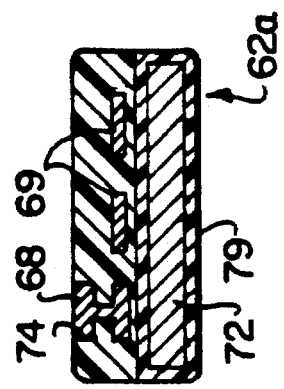
FIG. 5A is a cross-sectional view similar to FIG. 5 showing an alternative construction.

In general, the apparatus for mapping for a wall of a heart forming a ventricular chamber in the heart is comprised of an elongate flexible tubular member having a lumen extending therethrough and having proximal and distal extremities. A basket assembly is mounted on the distal extremity of the elongate flexible tubular member. The basket assembly is comprised of a plurality of circumferentially spaced-apart longitudinally extending arms having proximal and distal extremities. Means is provided for securing the proximal extremities of the arms to the distal extremity of the push-pull member. Means is provided for interconnecting the proximal extremities of the arms. The arms include members formed of a material having a recoverable strain in excess of 1.0% and having an outwardly bowed shape memory.

More particularly, the apparatus for ventricular mapping consists of a guiding catheter 21. The guiding catheter 21 consists of a shaft 22 having proximal and distal extremities 23 and 24. The shaft consists of a flexible elongate tubular member 26 formed of a suitable plastic materials such as PEBAX, a polyamide block copolymer and has a lumen 27 extending therethrough. The flexible elongate member has an outside diameter of 0.142" or 11 French and an inside diameter of 0.118" with a wall thickness of 0.012". A sleeve 28 formed of plastic extends over the flexible elongate tubular member 26 for the length thereof. A conventional Luer-type fitting 31 is mounted on the proximal extremity 23.

The apparatus of the present invention also comprises a pigtail catheter 36 which as shown in FIG. 2 consists of a shaft 37 having proximal and distal extremities 38 and 39. The shaft 37 is in the form of a flexible elongate tubular member formed of a suitable material such as plastic having a lumen 41 extending therethrough. The shaft 37 has a suitable outside diameter, as for example a 0.104" or 8 French and an inside diameter of 0.060" with a wall thickness of approximately 0.020".

The distal extremity 39 is tapered in cross-section so it has a smaller outside diameter of approximately 0.090". The distal extremity 39 is formed into a curved end portion in the form of a pigtail as shown for a purpose hereinafter described. A Luer-type fitting 46 is mounted on the proximal extremity 38 of the shaft 37.

The apparatus of the present invention also comprises a mapping catheter 51 which consists of a flexible shaft 52 having proximal and distal extremities 53 and 54. The flexible shaft 52 is in the form of an elongate flexible tubular member formed of a suitable plastic material such as a polyester. It is provided with a lumen 56 extending therethrough. The flexible elongate tubular member forming the shaft 52 can have a multilumen configuration with an outside diameter of approximately 0.105".

An electrode assembly 61 in the form of a basket is mounted on the distal extremity 54. It is provided with a plurality, as for example eight circumferentially spaced-apart longitudinally extending arms 62 having proximal and distal extremities 63 and 64. As shown, the arms 62 have an outwardly bowed shape memory and have their proximal extremities secured to the distal extremity 54 of the shaft 52. The distal extremities 64 of the arms 62 are interconnected as shown and are mounted in a hub 66 having a rounded forward extremity 67.

Figure 4:
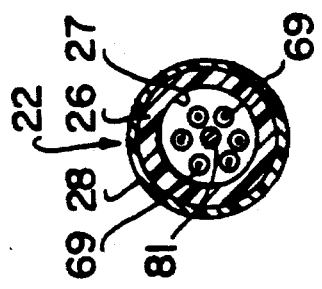
FIG. 4 is a cross-sectional view taken along the line 4—4 of FIG. 3.

A plurality of electrodes 68, as for example four are provided on the outer surface of each of the arms 2 and are spaced and longitudinally on the arms. The electrodes 68 are insulated from each other and are connected to conductors 69 in a suitable multi-conductor strip such as a ribbon cable or a flex-circuit strip 71 secured to elastic bands or members 72 (see FIG. 5) in a suitable manner such as by an adhesive (not shown). A tube 73 of a heat shrinkable material is slipped over each of the bands 72 and shrunk thereon by the application of heat to provide insulating material around the bands, and to firmly retain the flex strip 71 in engagement with the band 72. Cutouts 74 are provided in the heat shrink tube 73 to expose the electrodes 68 (see FIG. 4). The conductors 69 extend into the lumen 27 and extend rearwardly towards the proximal extremity 76 where they extend into and are connected to a connector 77 of a conventional type mounted in a handle 78 secured to the proximal extremity 53 of the shaft 52. The handle 78 is sized so that it is adapted to be grasped by the human hand. Thus, it is shown in the form of a cylinder having rounded ends as shown in FIG. 3.

Although not always necessary a pull element in the form of a flexible pull wire 81 can be provided which has its distal extremity secured in the hub 66. The pull wire 81 extends proximally centrally of the circumferentially spaced-apart arms 62 (see FIG. 3) into the flexible elongate tubular member (see FIG. 4) and has its proximal extremity secured to an inwardly extending protrusion 82 secured to a slider 83 slidably mounted in a slot 84 in the handle 78.

Figure 5:
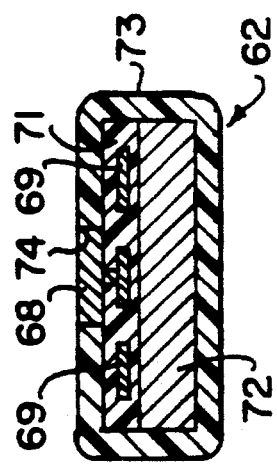
FIG. 5 is a cross-sectional view taken along the line 5—5 of FIG. 3.

An alternative arm construction 62a is shown in FIG. 5A. The band or member 72 is dipped in a polyimide to provide a coating 79 having a thickness of 0.0005" to 0.002". The flex strip 71 carrying the conductors 69 can be solvent bonded to the polyimide coating 79.

In accordance with the present invention, the bands or members 72 are formed of a material having a recoverable strain in excess of 1.0%. Such characteristics can be provided by certain metal alloys and plastics. The metal alloys are typically called shape-memory alloys which exhibit martensitic phase transformations. Such alloys include those which exhibit non-linear superelasticity (typically Ni—Ti with Ni at 49–51.5% atomic) and those which exhibit linear superelasticity (typically Ni—Ti in near equi-atomic composition which have been cold worked). Both the non-linear and linear superelastic alloys return to their shapes when stress is removed. The shape-memory alloys also include alloys which return to their initial shape when they are thermally activated by increasing the temperature to which they are subjected above the martensitic phase transformation for the alloy. Included in these thermally activated shape-memory alloys are those which exhibit a wide hysteresis of approximately 20° C. and larger. Such alloys can be stored while in a martensitic state and heated one time to transform to austenite. Cooling to the same starting temperature does not cause a reverse transformation to occur because of the wide hysteresis.

The composition and behavior of these shape-memory alloys are discussed in a book entitled "Engineering Aspects of Shape-Memory Alloys" published in 1990 by Butterworth-Heinemann, Ltd. of London and Boston.

The band is of rectangular cross-section (see FIG. 5) and can have dimensions such as a width ranging from 0.020" to 0.045" and preferably about 0.040" and a thickness ranging from 0.003" to 0.010" and preferably 0.006" to 0.008".

Plastics which have a recoverable strain in excess of 1.0% are thermoplastic-type polymers. For example, the Nylon family of polymers and polyurethanes can be used to fit such an application. Such materials can be heat set into the predetermined desired configuration as for example, the predetermined outwardly bowed configuration for the arms of the present invention. Satisfactory results also can be obtained by utilizing strips of sheet material which are heated and set into the desired shape to form the arms having the desired shape retention. A multi-layer construction also can be utilized which can be laminated together with an adhesive. For example, two layers of adhesive with three layers of polymer could be utilized and can be formed into the desired shape by the use of heat and pressure. In order to eliminate the need for adhesives, the polymers selected can have different melt temperatures. For example, a lower-melt polymer could be sandwiched between two higher-melt polymers and then heated under pressure in a mold to achieve the desired shape. The layered polymers would be melted together at their surfaces to prevent delamination. When utilizing such plastic layers for the arms, one of the plastic layers could serve to carry the conductors connected to the electrodes carried by the arms.

Figure 6:
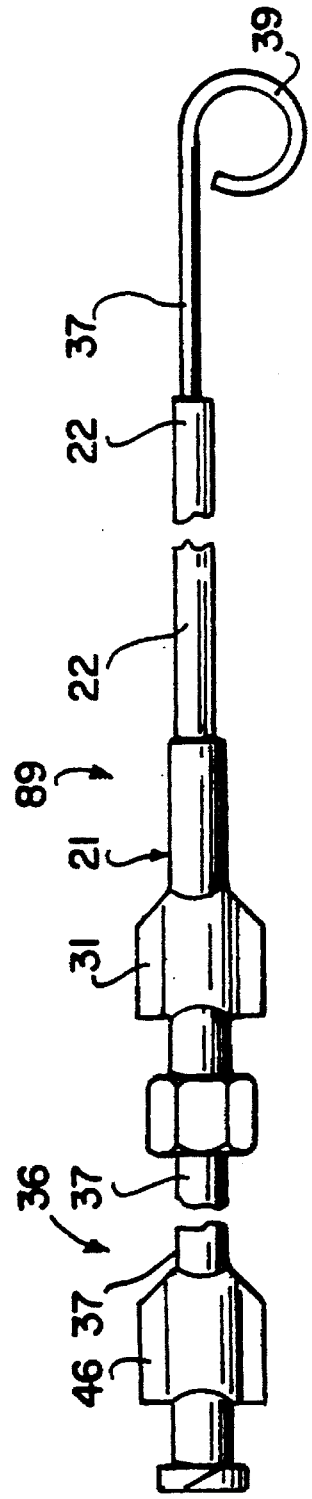
FIG. 6 is a side-elevational view showing the pigtail catheter disposed within the guiding catheter and ready for use.

Operation and use of the apparatus of the present invention in performing the method for ventricular mapping may now be briefly described as follows. Let it be assumed that it is desired to map the left ventricle 86 which is one of the chambers of a human heart 87 and is formed by a wall 88 as shown in FIGS. 7–11 of the drawings. Also let it be assumed that the apparatus of the present invention is to be introduced through the femoral artery of the patient. A cut down is made in the patient to expose the femoral artery. A sheath (not shown) is then placed in the cut out. The pigtail catheter 36 already has been introduced into the guiding catheter 21 to provide an assembly 89 as shown in FIG. 6 which is ready to be introduced into the introducer sheath (not shown). The pigtail catheter 36 with its pigtail 39 on its distal extremity provides a rounded forward extremity which is introduced into the sheath and then into the femoral artery followed by the guiding catheter 21. The assembly 89 is thus simultaneously advanced through the iliac artery up the descending aorta of the heart 87 and into the aortic arch 91. Advancement of the assembly is continued until the pigtail 39 is in close proximity to the aortic valve 92 as shown in FIG. 7. Thereafter, the guiding catheter 21 is held in a stationary position and the pigtail catheter 36 is advanced through the aortic valve 92. The rounded extremity provided by the pigtail catheter 36 serves to prevent any damage to the aortic valve 91 during this advancement of the pigtail catheter 36. The pigtail catheter 36 is then advanced into the left ventricle 86 until it reaches the apex 93 of the left ventricle 86 as shown in FIG. 8. As soon as the pigtail catheter 86 is at the apex 93 of the left ventricle 86, the guiding catheter 21 is advanced over the pigtail catheter 36 until it also reaches the apex 92 of the left ventricle 86. The pigtail catheter 36 is then withdrawn out of the guiding catheter 21 and completely removed from the body of the patient leaving the guiding catheter 21 in place with the tip or distal extremity of the guiding catheter 21 still at the apex 93 of the left ventricle as shown in FIG. 9.

Thereafter, the mapping catheter 51 is loaded into the guiding catheter 21. This is accomplished by compressing the basket assembly 61 into a cylindrical shape by hand and introducing it into the lumen 27 of the guiding catheter 21. The shaft 52 of the mapping catheter 51 with the basket assembly 61 at the distal extremity is then advanced in the guiding catheter 21 by use of the handle 78 until the basket assembly 61 has its hub 66 positioned at the distal extremity of the guiding catheter 21 and at the apex 93 of the left ventricle 86.

After this has been accomplished, the mapping catheter 51 is held in a stationary position and the guiding catheter 21 is progressively withdrawn to a position so that its distal extremity 24 is in the vicinity of the aortic valve 89. This causes progressive exposure of the basket assembly 61 so that it is deployed simultaneously as a guiding catheter 21 is withdrawn. The arms 62 of the basket assembly because of their stress activated memories of outwardly bowed configurations will immediately expand into contact with the wall 88 forming the left ventricle 86 so that the electrodes 68 carried on the outer surfaces thereof are moved into contact with the wall 88. If additional assurance is desired to be sure that all of the electrodes 68 are in contact with the heart wall 88, the slider 83 on the handle 78 is operated by a finger of the hand to pull on the pull wire 81 to further expand the basket assembly 61 while keeping the hub 66 of the basket assembly in contact with the apex 93.

The electrodes 68 are capable of sensing electrical signals which are generated in the wall of the heart. These electrical signals pass through the conductors 69 to the proximal extremity 53 to the connector 77 where they are connected to the electronics of the type hereinbefore described in U.S. Pat. No. 5,156,151 and may be accomplished without the use of multiplexing.

After the desired mapping operations have been carried out, the mapping catheter 51 can be removed by holding the guiding catheter 21 stationary with one hand and pulling the handle 78 and the mapping shaft 52 proximally to cause the basket assembly 61 to be progressively collapsed and drawn into the lumen 27 of the guiding catheter 21 until it is entirely disposed in the distal extremity 24 of the guiding catheter 21. Alternatively, the guiding catheter 21 can be advanced over the basket assembly 61 while holding the mapping catheter 51 in a stationary position to again cause collapse of the basket assembly and bring it within the lumen 27. After the basket assembly 61 is disposed within the lumen 27 of the guiding catheter 21, the assembly consisting of the mapping catheter 51 and the guiding catheter 21 can be removed from the patient. The introducer sheath can be removed and the cut down can be sutured in a conventional manner.

A similar procedure can be utilized for mapping the right ventricle 96 of the heart. In such a procedure, the guiding catheter and pigtail assembly 89 are advanced through the femoral vein to the vena cava of the heart until the pigtail 39 of the pigtail catheter 36 has been advanced to the right atrium. Typically the pigtail catheter can have a slight curvature placed in the distal extremity to facilitate advancing it through and across the tricuspid valve 97. After this has been accomplished the pigtail catheter 36 is advanced until it is in the apex of the right ventricle after which the guiding catheter 21 can be advanced to the apex. The pigtail catheter 36 can then be removed and the mapping catheter 51 inserted into the guiding catheter 21 into the appropriate position and the guiding catheter 21 withdrawn to expose the basket assembly 61 in a manner similar to that described in connection with mapping of the left ventricle.

From the foregoing it can be seen that an apparatus has been provided for mapping a chamber of the heart in which deployment of the basket assembly of the mapping catheter is automatic as soon as the guiding catheter is pulled proximally. The basket assembly deploys automatically because of the elastic properties of the strain recoverable material.

Figure 12:
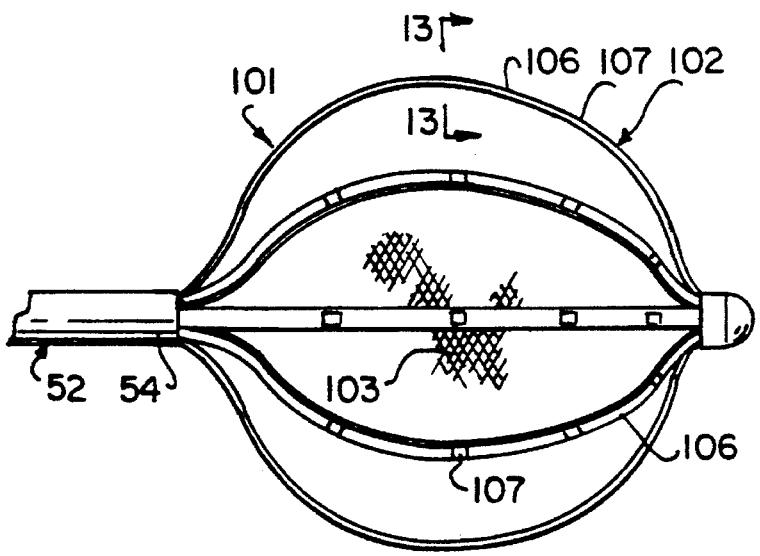
FIG. 12 is an enlarged partial side-elevational view of another embodiment of a mapping catheter incorporating the present invention.
Figure 13:
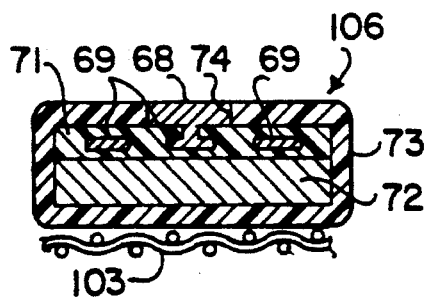
FIG. 13 is a cross-sectional view taken along line 13—13 of FIG. 12.

Another embodiment of a mapping catheter 101 incorporating the present invention is shown in FIGS. 12 and 13. The mapping catheter 101 is provided with a shaft 52 formed of a flexible tubular member of the type hereinbefore described having a distal extremity 54. A basket assembly 102 is provided which is comprised of a mesh or a braid 103 formed of a strain recoverable material as for example a superelastic material of the type hereinbefore described. The mesh or braid 103 is fabricated in a substantially ovoid shape as shown in the drawings and has a memory for this expanded shape. A plurality of circumferentially spaced-apart longitudinally extending arms 106 are secured to the exterior surface of the mesh or braid 103 and can be formed in the same manner as arms 62. The arms 106 are secured to the mesh or braid 103 by suitable means such as an adhesive (not shown). The arms 106 extend the length of the basket assembly 102 as shown in FIG. 12 and are provided with longitudinally spaced-apart electrodes 107.

This embodiment of the mapping catheter can be utilized in the same manner as the mapping catheter 51 hereinbefore described. The mesh 103 serves to ensure that a desired circumferential spacing of the arms 106 is maintained while the basket assembly is disposed in the ventricle of the heart. Thus, it can be assured that the angle between each pair of arms is a predetermined angle, for example an angle of 45° if eight arms are utilized. By providing a uniform predetermined spacing between the arms, it is much easier to establish the location where electrical signals being monitored by the electrodes 68 are positioned in the wall of the heart.

Figure 14:
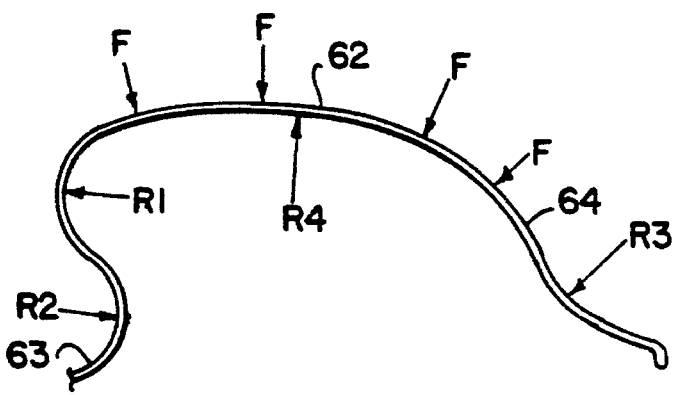
FIG. 14 is a partial side-elevational view of one of the arms of a basket assembly showing the manner in which forces are applied to the arms of the basket assembly during commencement of systolic movement of the heart.
Figure 15:
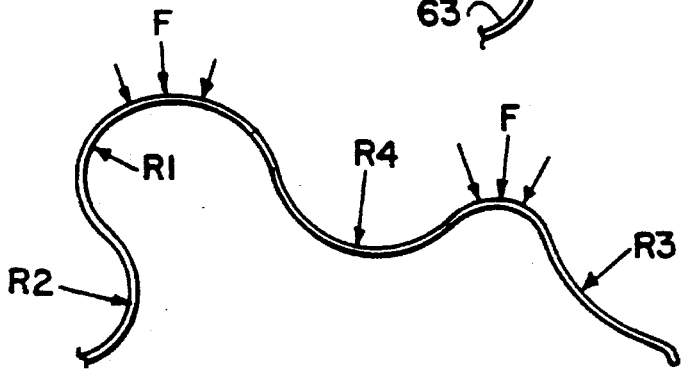
FIG. 15 is a partial side-elevational view of the arm shown in FIG. 4 after it has been compressed during systole and showing how a waist is formed in the arm.
Figure 16:
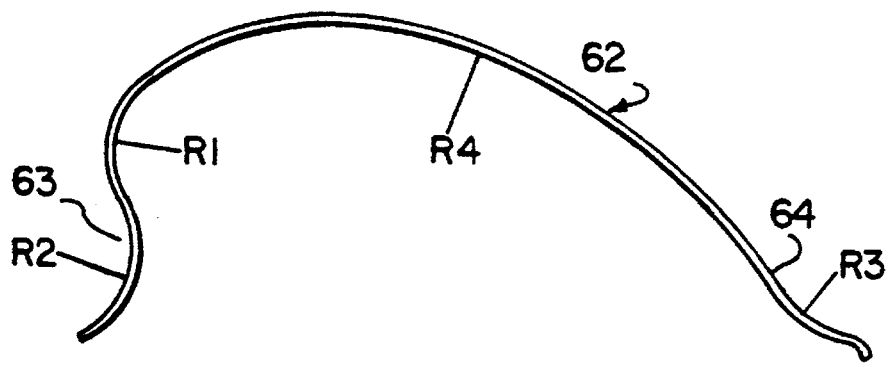
FIG. 16 is a partial side-elevational view of a basket assembly with arms provided therein to overcome wasting.

In connection with the basket assemblies 61 and 102 hereinbefore described, it has been found that it may be desirable to form the arms in a particular way in order to eliminate waisting. FIGS. 14 and 15 depict the manner in which waisting occurs during movement of the wall of the heart during pumping of blood operation between diastole and systole. Thus, by way of example a typical arm 62 is shown in FIG. 14 positioned in the left ventricle of the heart shortly after the heart has moved into an expanded or diastole condition. The typical arm 62 in this condition of the heart has curvatures of small radii formed in the proximal extremity 63 and the distal extremity 64, as for example curves of radii R1 and R2 in the proximal extremity 63 as shown in FIG. 14 and a curve shown with a radius R3 in the distal extremity 64 as shown in FIG. 14. Between the proximal extremity 63 and the distal extremity 64 there is a curve of a large radius R4 as also shown in FIG. 14. The forces being applied by the heart wall are identified by the arrows F as shown in FIG. 14. As the heart wall moves towards the systole condition, the wall of the heart finds that it requires greater forces to cause bending of the proximal and distal extremities of the arms 63 and 64 in comparison to the intermediate portion because these portions of the arm have a smaller radii than the radius of the large curvature identified by the radius R4. It is believed that this is the case because the proximal and distal extremities 63 and 64 have a greater column strength than the intermediate portion. In other words, the intermediate portion represented by the radius R4 has a longer unsupported length than the proximal and distal extremities 63 and 64. It has been found that these differences in column strength cause the buckling or an inwardly bowed movement of the intermediate portion of the typical arm represented by the radius R4 to a position shown in FIG. 15 which can be considered as forming an hour glass-like shape that can be characterized as wasting. This is similar to the waist of a human figure, which can be characterized as the narrower part of a body or structure. This wasting is undesirable because it causes the intermediate portion of the typical arm 62 represented by the curve R4 to move out of contact with the wall of the heart. This also causes the electrodes carried by that portion of the arm to move out of contact with the wall of the heart. Thus signals will not be picked up by those electrodes during at least portions of the heart cycle in moving from the diastole to systole and from systole to diastole.

In order to overcome this potential problem, the proximal and distal extremities 63 and 64 of the arms are treated or formed to reduce the cross-sectional area of those portions of the arms to thereby decrease their column strength whereby lesser forces are necessary to cause bending or deflection of the proximal and distal extremities 63 and 64 while leaving the forces required to bend the intermediate portion the same so that wasting of the arms will not occur during movement of the heart between diastole and systole.

Figure 17:
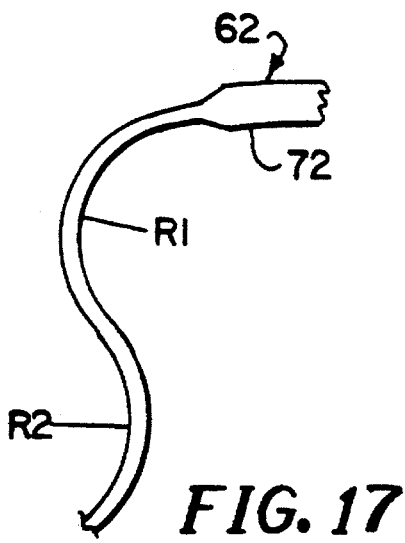
FIG. 17 is an enlarged cross-sectional view of the proximal extremity of the arms shown in FIG. 16.
Figure 18:
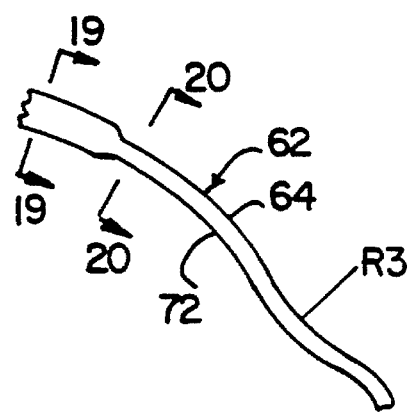
FIG. 18 is an enlarged side-elevational view of the distal extremity of the arm shown in FIG. 16 incorporating the present invention.
Figure 19:
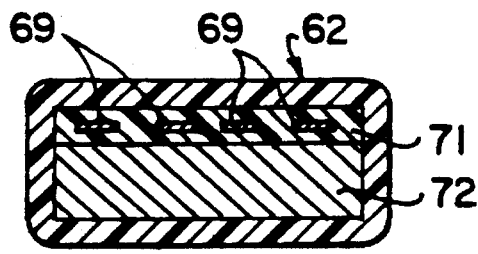
FIG. 19 is a cross-sectional view taken along the line 19—19 of FIG. 18.
Figure 20:
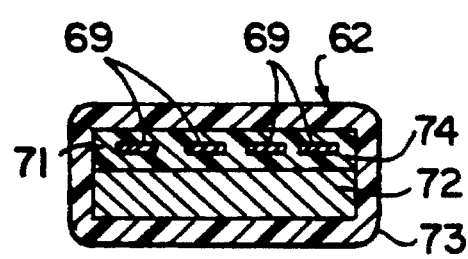
FIG. 20 is a cross-sectional view taken along the line 20—20 of FIG. 18.

One construction providing these weakened proximal and distal extremities 63 and 64 can be accomplished by chemically etching the proximal and distal extremities so they have reduced cross-sectional areas as shown in FIGS. 17 and 18. Assuming that a superelastic material such as the nickel-titanium alloy hereinbefore described is utilized, one of the proximal extremities 63 and 64, as for example the proximal extremity 63 and thereafter the distal extremity 64 can be placed in an acid mixture of a type well known to those skilled in the art. This can be accomplished at temperature ranging from 10° to 60° C. while constantly agitating the acid for a suitable period of time ranging from 2 to 20 minutes and preferably about 10 minutes to cause uniform etching of the proximal extremity 63 to occur so that it is of reduced cross-sectional area as shown in FIG. 17. As soon as this has been accomplished, the same procedure can be utilized for the distal extremity 64 to provide the band 72 of reduced cross-sectional area as shown in FIG. 18. Assuming that the band 72 has a cross-sectional area as hereinbefore described, both dimensions can be reduced by a suitable amount, as for example 0.002" the original dimensions of 0.006" and 0.04" causing a reduction in cross-sectional area of approximately 30%. A reduction in cross-sectional area ranging from 20 to 70% may be appropriate.

It should be appreciated that any desired reduction in cross-sectional area can be achieved in this manner by increasing or decreasing the length of time in which the proximal and distal extremities 63 and 64 are immersed in the acid mixture bath. It also should be appreciated that a tapering of this portion of reduced area can also be accomplished by gradually withdrawing the extremity from the nitric acid solution while the etching is taking place so that a progressive or tapered configuration can be provided for the extremities of the arms. Alternatively the proximal and distal extremities can be weakened by coining or stamping to provide the reduced cross-sectional area. Also to provide weakening of the extremities of the arms 62 the bands 72 can be made shorter so that they terminate before the extremities. Such weakening of the extremities can also be provided by localized heat treatment or annealing.

It has been found by weakening the extremities of the arms 62 by forming the band 72 in a manner similar to that hereinbefore described all portions of the arms 62 will remain substantially in engagement with the wall of the heart during the pumping of the heart in moving between diastole and systole. This greatly enhances the reliability of the data being collected during a mapping operation of a ventricle of the heart.

Although the foregoing description of the basket assemblies 61 and 102 have primarily been described in conjunction with the use of shape-memory alloys which exhibit nonlinear superelasticity and linear superelasticity it should be appreciated that shape-memory alloys which are thermally activated can be utilized in conjunction with the present invention. For example, thermally-activated shape memory alloys which are activated at body temperature can be utilized for causing the arms 62 to expand into engagement with the wall of the heart after the arms have been deployed from the guiding catheter 21. It also should be appreciated that if desired, electrical energy can be supplied directly or indirectly to the bands 72 to heat the bonds to cause them to be thermally activated to attempt to assume their memorized positions.

More in particular, a ventricular mapping apparatus 121 which utilizes a thermally activated shape memory alloy is shown in FIG. 21. As shown therein, it consists of a mapping and ablation catheter 122 which is connected by a cable 123 to a constant current power supply 124. The constant current power supply 124 is provided with a case 126. An on/off switch 127, a digital display 128 and a knob 129 are mounted on the case 126. The knob 129 is used for controlling the amount of current supplied from the power supply 124 to the catheter 122.

A schematic diagram of the constant current power supply 124 is shown in FIG. 22. A DC positive voltage is supplied to a potentiometer 127 which is connected between V+ and ground. It is provided with a wiper arm 128 which is connected to the knob 129 provided on the case 126. The wiper arm 128 is connected to the plus terminal of an operational amplifier 129 that is connected as a voltage follower. Its output is supplied to a conventional power transistor Q1 which is also connected to the V+ supply and supplies its output to the arm 131 of a basket 132 of the catheter 122 with each of the arms 131 having a band 136 formed of a shape memory alloy of the type hereinbefore described. This band 136 is represented as a resistor in FIG. 22 and has one end connected to the output of the power transistor Q1 and has the other end connected to the negative input of the operational amplifier 129. The negative terminal of the operational amplifier is connected to ground through a sensing resistor 137 which can be of suitable value as for example one ohm.

The circuitry shown in FIG. 22 makes it possible to supply a constant current to the band 136 of the shape memory alloy regardless of the value or change in resistance of the band 136. The operational amplifier 129 controls the transistor Q1 to cause it to supply a voltage which is sufficient to cause a constant current as determined by the position of the wiper 128 on the potentiometer 127 in the arms 136 to cause bowing of the arms and to provide a desired yieldable stiffness in the arms so that the arms remain in contact with the wall of the heart during beating of the heart.

The catheter 122 consists of a flexible elongate tubular member 141 of the type hereinbefore described and is provided with a proximal extremity 142 and a distal extremity 143. The proximal extremity 142 is secured to a handle 146 of the type hereinbefore described which is connected to the cable 123. The basket 132 hereinbefore described is mounted on the distal extremity 143 of the flexible elongate tubular member 141 and is provided with a rounded tip 148. The basket 132 is provided with a plurality of circumferentially spaced apart arms 131.

Figure 24:
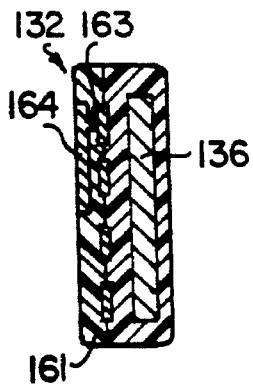
FIG. 24 is a cross-sectional view taken along the line 24—24 of FIG. 23.

By way of example, the basket 132 can be formed from a flexible plastic sheet 151 having serially connected arms 131. As shown in FIGS. 23 and 24, the sheet 151 by way of example carries eight bands 136 of the shape memory alloy material hereinbefore described which are spaced apart on the rectangular sheet 151. As can be seen in FIG. 23, the bands 136 are serially interconnected by end portions 136a and 136b to provide a serpentine pattern which has one end connected to a terminal 153 and has the other end connected to a terminal 154. The terminals 153 and 154 are connected by conductors (not shown) extending through the flexible elongate member 141 to the power supply 124 through the cable 123 and the handle 146. The sheet 151 is provided with a plurality of slits 156 extending longitudinally of the sheet 151 which are spaced apart and parallel to provide the separate arms 131 which are spaced apart circumferentially when the sheet 151 is wrapped into a cylinder to form the basket 132.

Each arm 131 is provided with a multi-conductor strip in the form of a flex strip 161 that carries a plurality of conductors 162 embedded therein and in which feed throughs 163 make contact to electrodes 164 carried thereby and which are exposed on the outer surface of the arm 132 in the same manner as hereinbefore described with connection to the previous embodiments.

With the arrangement shown in FIGS. 23 and 24, all eight of the arms 131 of the basket 132 are connected in series which increases the resistance seen by the power supply 124. Thus makes it possible to deliver the necessary electrical energy to the basket assembly more efficiently than would be the case if the arms were connected in parallel. The arms if in parallel would have relatively lower resistance and in combination would require a much higher total current to be delivered by the power supply. This increased current flow could cause undue undesirable heating in the flexible elongate tubular member 141 of the catheter.

Figure 25:
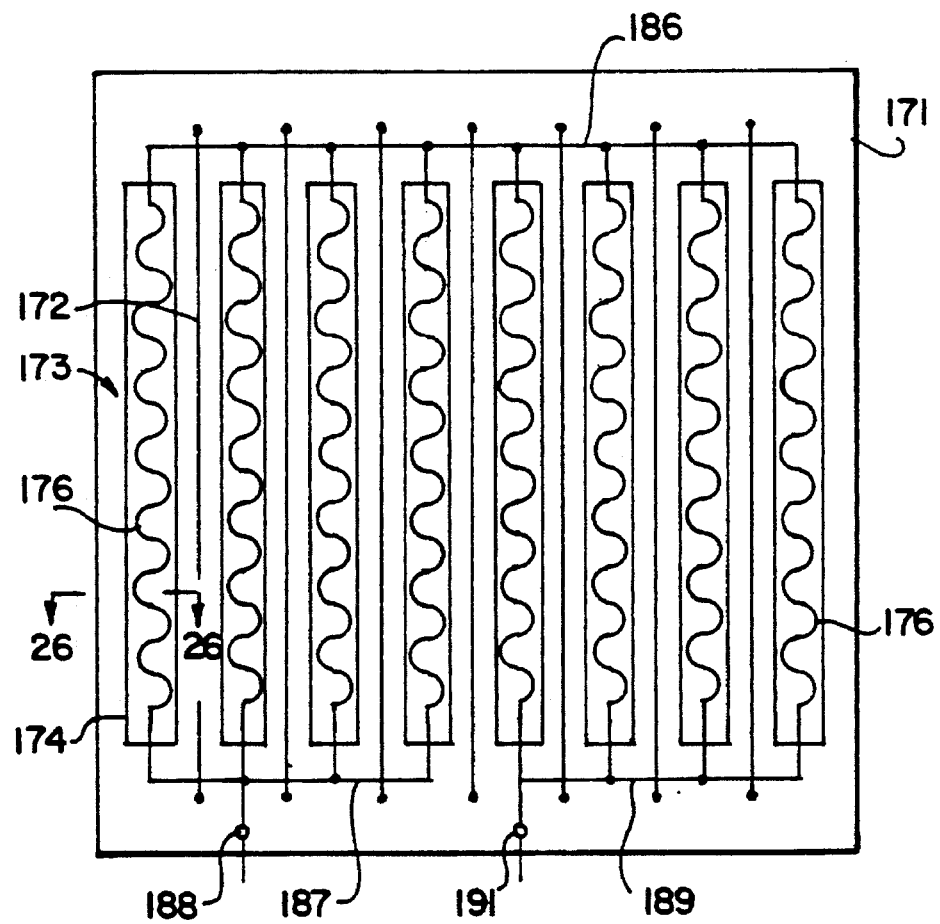
FIG. 25 is a plan view of an alternative embodiment of a sheet of plastic for use in making a basket for the apparatus shown in FIG. 21.
Figure 26:
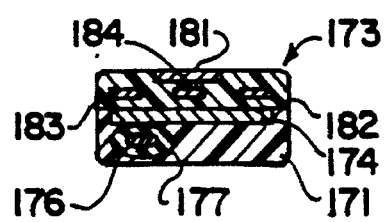
FIG. 26 is a cross-sectional view taken along the line 26—26 of FIG. 25.

An alternative embodiment for the basket 132 shown in FIG. 21 in shown in FIGS. 25 and 26. As shown therein it consists of a sheet 171 of a suitable plastic material which has been provided with a plurality of longitudinally extending parallel spaced apart slits 172 to provide a plurality of arms 173 that have bands 174 provided therein formed of a shape memory alloy of the type hereinbefore described and which is encapsulated by the plastic forming the sheet 171 as shown in FIG. 26. Also encapsulated within the plastic 171 is a heating element 176 extending longitudinally of the band 174 and being in relatively close proximity thereto but being insulated therefrom by an insulating layer 177 that serves to electrically isolate the heating conductor or element 176 from the band 174 which also is formed of a conducting material. The heating element 176 can be disposed in any position longitudinally the arms in relatively close proximity to the bands 174 so that when energy is supplied through the heating elements 176, the heat is transferred by conduction to the band 174 to cause the band to attempt to assume the bowed configuration that is in its memory. As in previous embodiments of the arms for the basket 132, the arms 172 are provided with a plurality of longitudinally spaced apart electrodes 181 which are carried by a multiple conductor strip as for example the flex strip 182 which has embedded therein a plurality of longitudinally extending conductors 183 with each of the electrodes 181 being connected by a feedthrough 184 to one of the leads 183.

As can be seen, the heating element 166 can have a serpentine pattern travelling along the length of the arm as shown in FIG. 25 and can extend across from side to side of the band 174. As also shown in FIG. 25, the heating elements 176 of the eight arms 172 are connected into two groups of four in which the distal extremities are all interconnected by a connector 186 and in which the proximal ends of one set of heating elements 176 are interconnected by a conductor 187 to a terminal 188 and the proximal ends of the heating elements 176 of the other set are connected by a conductor 189 to a terminal 191. Such a wiring arrangement is desirable in that it makes it possible to supply electrical energy to the heating elements 176 from terminals 188 and 191 at the proximal extremity of the basket 132. This facilitates making connections (not shown) to the conductors which extend through the tubular elongate member 141 and which are connected to the handle 146 and through the cable 123 to the power supply 124. In addition by placing the two sets of four arms in a series, the resistivity is increased to decrease the current flow through the heating elements 176.

Although the arms of the baskets hereinbefore described have assumed that stress activated and thermally activated members utilized in the arms extend substantially the entire length of arms, it should be appreciated that short segments of these members can be provided and placed in appropriate positions in the arms to achieve the desired shape and/or stiffness. Such cross section as for example rectangular or circular. Also such members can form a part of a composite construction in which a plastic can be used as a carrier.

From the foregoing it can be seen that there has been provided a catheter which has the basket assembly provided with thermally-activated shape memory elements to cause the same to be bowed outwardly to attempt to assume their predetermined memory when thermal energy is supplied to the bands 174 either by passing current directly through the strips 136 to heat the same or by indirectly heating the bands 174 by supplying electrical energy in the form of a current to the heating element or elements 176.

Although the ventricular mapping and ablation apparatus hereinbefore described has been described primarily in conjunction with mapping potentials in the wall of the heart, it should be appreciated that if desired, electrodes can be provided on the arms which can be utilized for performing ablations or adhesions in the wall of the heart after the mapping has indicated a promising area for performing such a procedure.

From the foregoing it can be seen that there has been provided a new and improved apparatus and method for use in ventricular mapping which greatly increases the reliability of the mapping procedure.

What is claimed is:

1. An apparatus for mapping electrical signals arising in a wall of a heart forming a chamber in the heart, comprising a flexible shaft having proximal and distal extremities and a basket assembly, the basket assembly comprising a plurality of circumferentially spaced-apart longitudinally extending arms having proximal and distal extremities and having an outwardly facing surface, means securing the proximal extremities of the arms to the distal extremity of the shaft, each of said arms including a member formed of an elastic material having a recoverable strain of more than 1.0% and having an outwardly bowed shape memory, a plurality of electrodes on each of the arms, means carried by each of said arms for mounting said electrodes in spaced-apart positions longitudinally of each arm so that they are insulated from each other and are exposed solely in a direction extending from the outwardly facing surface of each arm and adapted to face only the wall of the chamber and conductor means on the arms connected to the electrodes carried by the arm for conducting electrical signals detected by the electrodes.

2. Apparatus as in claim 1 further including a guiding catheter comprising a flexible elongate tubular member having a lumen extending therethrough and wherein said basket assembly is compressible so that it can be, said shaft being removably inserted in said lumen moved out of and into the lumen of the flexible elongate tubular member, said basket assembly being capable springing into its outwardly bowed shape memory upon discharge from the lumen of the guiding catheter.

3. Apparatus as in claim 2 wherein said member in each of said arms is formed of a shape-memory material.

4. Apparatus as in claim 3 wherein said shape-memory material is a stress-activated material.

5. Apparatus as in claim 3 wherein said shape-memory material is a thermally-activated material.

6. Apparatus as in claim 5 together with means carried by the arms for supplying heat to the member of each of the arms.

7. Apparatus as in claim 6 wherein said means for supplying heat includes means for supplying electrical energy to the members of each of the arms so that electrical current flows through the members to heat the same.

8. Apparatus as in claim 7 wherein said means for supplying electrical energy to the members includes means for connecting at least certain of said members in series electrically.

9. Apparatus as in claim 6 wherein said means for supplying heat includes a heating element disposed in close proximity to the member but insulated therefrom and means for supplying electrical energy to the heating element.

10. Apparatus as in claim 9 wherein said means for supplying electrical energy to the heating element includes means for connecting at least certain of said heating elements in series electrically.

11. Apparatus as in claim 1 wherein said member is formed of a plastic.

12. Apparatus as in claim 1 wherein said member is in the form of a band having a width which is substantially greater than its thickness.

13. Apparatus as in claim 12 wherein said band is substantially rectangular in cross section.

14. An apparatus for mapping electrical signals arising in a wall of a heart forming a chamber in the heart, comprising a flexible shaft having proximal and distal extremities and a basket assembly, the basket assembly comprising a plurality of circumferentially spaced-apart longitudinally extending arms having proximal and distal extremities, means securing the proximal extremities of the arms to the distal extremity of the shaft, each of said arms including a member formed of an elastic material having a recoverable strain of more than 1.0% and having an outwardly bowed shape memory, at least one electrode provided on each of the arms and conductor means on the arms connected to the electrodes carried by the arm for conducting electrical signals detected by the electrodes, said member being in the form of a band having a width which is substantially greater than its thickness, said band being enclosed within an insulating layer to provide an enclosed band, said conductor means connected to said electrodes in said arms being carried in a multiple conductor strip secured to the enclosed band.

15. Apparatus as in claim 14 wherein said electrodes are carried by the multiple conductor strip.

16. Apparatus as in claim 15 wherein said multiple conductor strip is in the form of a flex strip, said flex strip being provided with openings and wherein said electrodes are exposed through said openings in the flex strip.

17. In an apparatus for mapping electrical signals arising in a wall of a heart forming a chamber in the heart, comprising a flexible shaft having proximal and distal extremities and a basket assembly, the basket assembly comprising a plurality of circumferentially spaced-apart longitudinally extending arms having proximal and distal extremities and having an outwardly facing surface, means securing the proximal extremities of the arms to the distal extremity of the shaft, each of said arms including a member formed of an elastic material having a recoverable strain of more than 1.0% and having an outwardly bowed shape memory, a plurality of electrodes on each of the arms, means carried by each of said arms for mounting said electrodes in spaced-apart position longitudinally of each arm and so that they are flush with the outwardly facing surface of each arm and conductor means on the arms connected to the electrodes carried by the arm for conducting electrical signals detected by the electrodes, said arms having a column strength and thickness, the proximal and distal extremities of the arms having a reduced cross-sectional area to reduce the column strength and stiffness of the proximal and distal extremities to help ensure that the electrodes carried by the arms are retained in engagement with the wall of the heart during movement of the wall as pumping of the heart occurs.

18. A mapping catheter for mapping electrical signals arising in a wall of a heart forming a chamber in the heart, comprising a flexible elongate tubular member having proximal and distal extremities and having a cylindrical configuration, a basket assembly comprised of a plurality of circumferentially spaced-apart longitudinally extending arms having proximal and distal extremities, means securing the proximal extremities of the arms to the distal extremity of the elongate flexible tubular member, said arms having outer surfaces, electrodes carried by the outer surfaces insulated from each other and being exposed solely in a direction extending from the outer surfaces and conductor means connected to the electrodes and carried by the arms for conducting electrical signals detected by the electrodes and extending through the flexible elongate tubular member to the proximal extremity thereof, each of said arms including a member of an elastic material having a recoverable strain of more than 1.0% and having an outwardly bowed shape memory, said arms being compressible so that they have a cylindrical configuration which corresponds generally to the cylindrical configuration of the elongate flexible tubular member.

19. A mapping catheter as in claim 18 wherein said elastic material is a shape-memory alloy.

20. A mapping catheter as in claim 18 wherein said elastic material is a plastic.

21. A mapping catheter for mapping electrical signals arising in a wall of a heart forming a chamber in the heart, comprising a flexible elongate tubular member having proximal and distal extremities, a basket assembly comprised of a plurality of circumferentially spaced-apart longitudinally extending arms having proximal and distal extremities, means securing the proximal extremities of the arms to the distal extremity of the elongate flexible tubular member, said arms having outer surfaces, electrodes carried by the outer surfaces and conductor means connected to the electrodes and carried by the arms for conducting electrical signals detected by the electrodes and extending through the flexible elongate tubular member to the proximal extremity thereof, each of said arms including a member of an elastic material having a recoverable strain of more than 1.0% and having an outwardly bowed shape memory, said arms being compressible so that they have a cylindrical configuration which corresponds generally to the cylindrical configuration of the elongate flexible tubular member, said elastic material being a shape-memory alloy, said shape-memory alloy having a substantially rectangular cross-section to form a band, said electrodes and said conductor means being in the form of a multiple conductor strip secured to said band.

22. A mapping catheter as in claim 21 wherein each of said arms includes a sleeve formed of an insulating material extending over said band and means securing said multiple conductor strip to retain said multiple conductor strip in engagement with said band, said strip having openings therein to expose said electrodes so that they can contact the wall of the heart.

23. A catheter for mapping a wall of an organ comprising a flexible elongate tubular member having proximal and distal extremities and having a cylindrical configuration, a basket assembly comprised of a plurality of circumferentially spaced-apart longitudinally extending arms having proximal and distal extremities and intermediate portions, said proximal and distal extremities having a stiffness and including means for reducing the stiffness of the proximal and distal extremities, means securing the proximal extremities of the arms to the distal extremity of the elongate flexible tubular member, said arms having outer surfaces, electrodes carried by the outer surfaces and being flush with the outer surfaces and conductors connected to the electrodes and carried by the arms and extending through the flexible elongate tubular member to the proximal extremity thereof, said arms having an outwardly bowed shape memory and being compressible so that they can have a cylindrical configuration which conforms generally to the cylindrical configuration of the elongate flexible tubular member.

24. An mapping catheter comprising a flexible elongate tubular member having proximal and distal extremities and a cylindrical configuration, a basket assembly comprised of a plurality of circumferentially spaced-apart longitudinally extending arms having proximal and distal extremities and intermediate positions, said proximal and distal extremities being of reduced cross-sectional area in comparison to the intermediate portions, means securing the proximal extremities of the arms to the distal extremity of the elongate flexible tubular member, said arms having outer surfaces, electrodes carried by the outer surfaces and conductor means connected to the electrodes and carried by the arms and extending through the flexible elongate tubular member to the proximal extremity thereof, said arms having an outwardly bowed shape memory and being compressible so that they can have a cylindrical configuration which conforms generally to the cylindrical configuration of the elongate flexible tubular member, each of said arms including a band formed of a material having a recoverable strain of more than 1% and having a substantially rectangular cross-section, said electrodes and said conductor means being in the form of a multiple conductor strip secured to said band.

25. A mapping catheter as in claim 24 wherein said band is covered with a layer of insulating material.

26. A mapping catheter as in claim 24 wherein each of said arms includes a sleeve formed of a heat-shrinkable insulating material extending over said band and said multiple conductor strip to retain said multiple conductor strip in engagement with said band, said sleeve having openings therein to expose said electrodes so that the electrodes can contact the wall of the heart.

27. A method for carrying out a mapping operation of a wall of a heart which forms a chamber in the heart of a patient and having a valve opening into the chamber by using a guiding catheter having a distal extremity, a pigtail catheter having a distal extremity and a mapping catheter of the type having a shaft carrying a basket assembly including a plurality of circumferentially spaced-apart longitudinally extending arms with electrodes carried by the arms and with the arms having an outwardly bowed shape memory comprising inserting the pigtail catheter into the guiding catheter to form a catheter assembly in which the pigtail catheter is positioned in the guiding catheter so that the distal extremity of the pigtail catheter extends beyond the distal extremity of the guiding catheter, introducing the catheter assembly into the patient so that the pigtail catheter leads the guiding catheter as the catheter assembly is advanced into the heart until the pigtail catheter is in the vicinity of the valve, holding the guiding catheter stationary while advancing the pigtail catheter through the valve of the heart and then further advancing the pigtail catheter until the distal extremity of the pigtail catheter reaches the apex of the chamber of the heart, holding the pigtail catheter in a stationary position while advancing the distal extremity of the guiding catheter through the valve of the heart into the chamber so that the distal extremity of the guiding catheter is disposed at the apex of the chamber of the heart, withdrawing the pigtail catheter from the guiding catheter while holding the guiding catheter stationary so that its distal extremity remains in the vicinity of the apex of the chamber of the heart, introducing the basket assembly of the mapping catheter into the guiding catheter, advancing the mapping catheter in the guiding catheter until the basket assembly of the mapping catheter is at the distal extremity of the guiding catheter adjacent to the apex of the chamber of the heart in which the guiding catheter is disposed, progressively withdrawing the guiding catheter while holding the mapping catheter stationary and permitting the basket assembly to progressively emerge from the guiding catheter and to expand into engagement with the wall forming the chamber of the heart until the basket assembly has been expanded while retaining the distal extremity of the guiding catheter within the chamber of the heart just distal of the valve of the heart in which it is disposed, conducting mapping operations with the basket assembly while expanded, causing the basket assembly to enter the guiding catheter and then withdrawing the guiding catheter and the basket assembly from the patient.

28. A method as in claim 27 wherein during the withdrawal of the basket assembly, the withdrawal of the basket assembly is accomplished by advancing the guiding catheter over the expanded basket assembly while holding the mapping catheter in a stationary position.

29. A method as in claim 27 wherein the mapping catheter is provided with a pull wire for causing further expansion of the basket assembly together with the step of pulling on the pull wire to further expand the basket assembly after the basket assembly has been deployed.

* * * * *